United States Patent [19]

Treace

[11] 4,281,419
[45] Aug. 4, 1981

[54] MIDDLE EAR OSSICULAR REPLACEMENT PROSTHESIS HAVING A MOVABLE JOINT

[75] Inventor: Harry T. Treace, Forest Hill, Tenn.

[73] Assignee: Richards Manufacturing Company, Inc., Memphis, Tenn.

[21] Appl. No.: 101,774

[22] Filed: Dec. 10, 1979

[51] Int. Cl.³ .......................... A61F 1/24; A61F 1/18
[52] U.S. Cl. ........................................ 3/1.9; 128/92 C
[58] Field of Search ...................... 3/1.9, 1; 128/92 C

[56] References Cited

U.S. PATENT DOCUMENTS

| | | | |
|---|---|---|---|
| 3,473,170 | 10/1969 | Haase et al. | 3/1 |
| 3,722,003 | 3/1973 | Walchle | 3/1 |
| 3,909,852 | 10/1975 | Homsy | 3/1.9 |
| 4,052,754 | 10/1977 | Homsy | 3/1.9 |
| 4,169,292 | 10/1979 | Grote | 3/1.9 |

*Primary Examiner*—Ronald L. Frinks
*Attorney, Agent, or Firm*—Robert D. Yeager

[57] ABSTRACT

An improvement in an otic prosthesis of the type used in ossicular reconstruction of the sound-conducting mechanism of the middle ear is provided. The improvement comprises a movable joint which connects a head portion and a shaft portion whereby there is provided a flexible, variably angled prosthesis, which can be readily set in position in the middle ear against the tympanum during surgical implantation. The movable joint permits the so-connected shaft portion to move in at least a single plane normal to the head portion and can itself be readily set against either retained bony elements of the sound-conducting mechanism or against tissue grafted into the aperture (oval window) between the middle and the inner ear. The movable joint is responsive to tympanic vibrations and the prosthesis exerts a minimized pressure on the tympanum during surgical implantation and thereafter it also resists dislodgment within or extrusion from the middle ear. The mounting means is characteristically a ball-and-socket joint whereby the ball is attached to the shaft and the socket to the head.

The head portion of the prosthesis is preferably constructed entirely of a porous, biocompatible material which enables rapid tissue ingrowth. The shaft portion, in a preferred embodiment, is also formed of the same porous material thus enabling tissue ingrowth at the oval window-engaging end of the device.

7 Claims, 8 Drawing Figures

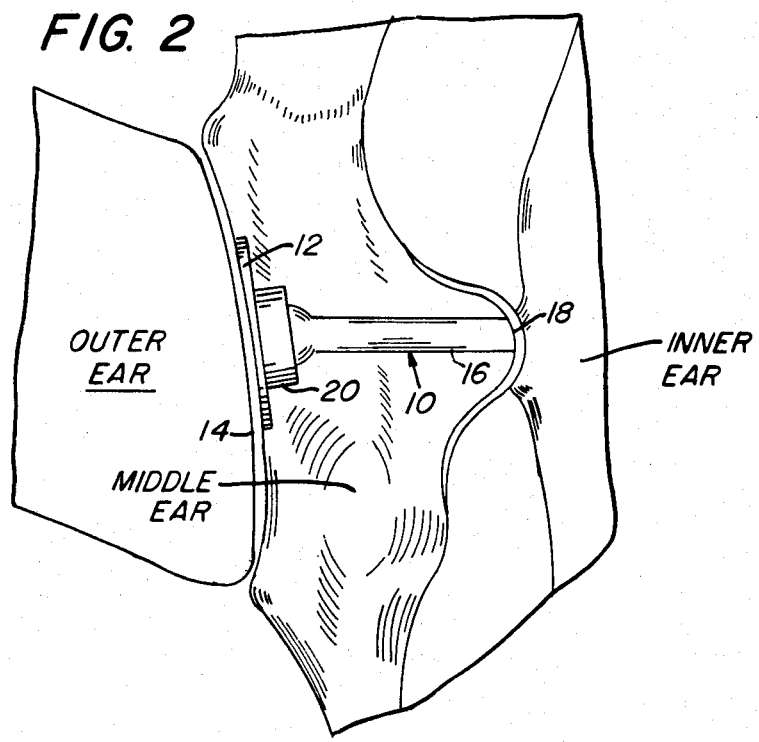
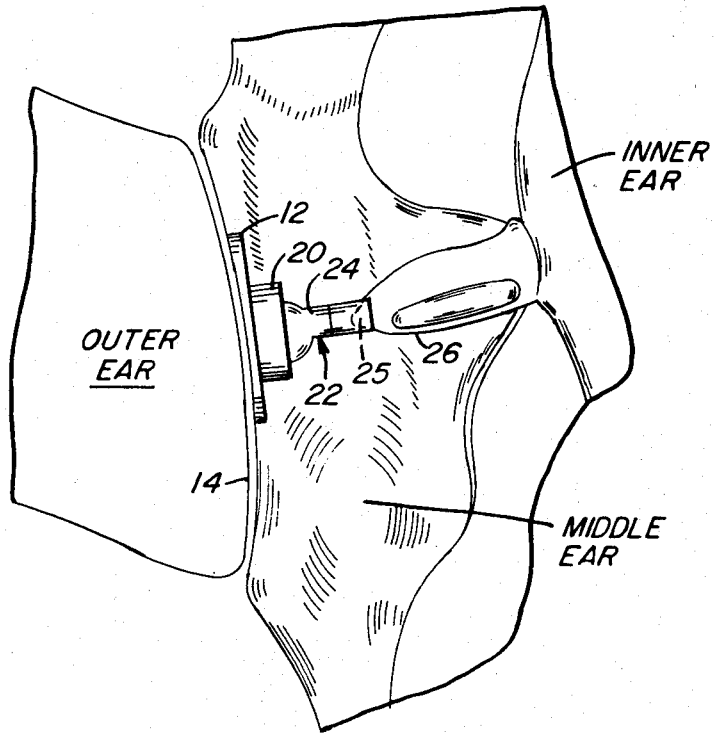

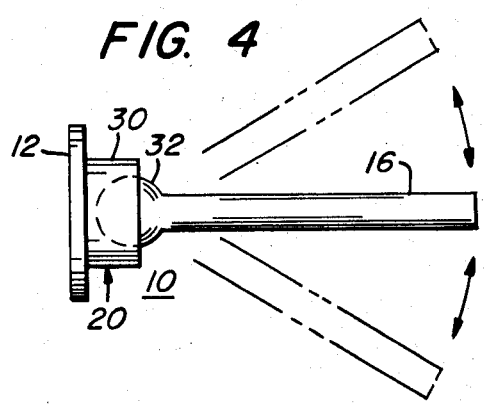
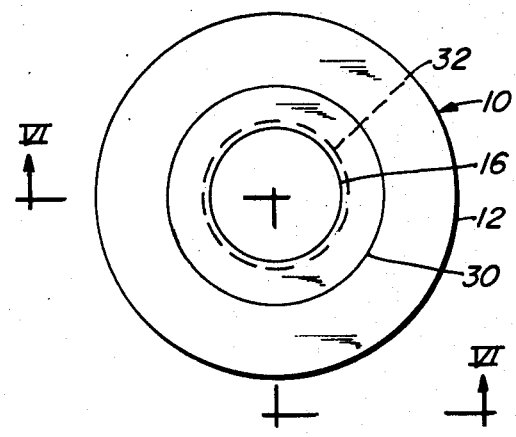
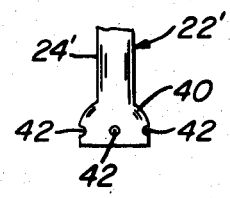
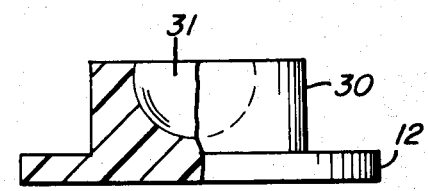
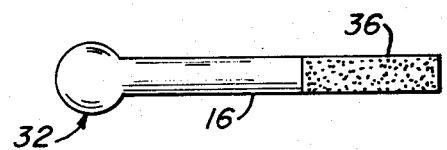

MIDDLE EAR OSSICULAR REPLACEMENT PROSTHESIS HAVING A MOVABLE JOINT

BACKGROUND OF THE INVENTION

1. Field Of The Invention

This invention relates to otic prosthesis; more particularly to ossicular replacement prosthesis for the middle ear.

2. Description Of The Prior Art

Reconstruction of the sound-conducting mechanism of the middle ear by surgical implantation of biocompatible prostheses is well known. FIG. 1 of the drawings is a schematic representation of the natural mechanism for transmitting vibrations of the eardrum (tympanum) to the sound-producing organs of the inner ear which are located behind the aperture (oval window) between the middle and inner ears. The mechanism includes three tiny bones called the malleus, the incus and the stapes, which move in response to the vibration of the tympanum. When disease or advanced infection of the middle ear occurs, excessive bone growth around or degeneration of these tiny bones can prevent their movement with a consequent loss of hearing. Hearing may be restored by the removal of two or three of these bones and the surgical implantation of a vibration-transmitting prosthesis.

Ossicular replacement prostheses take two basic forms: (1) When all three bones are removed, the prosthesis must span between the tympanum and the oval window or footplate and thus is called a total ossicular replacement prosthesis. Typically, the prosthesis is a one-piece device having a broad, thin head portion resting against the tympanum and a rigidly connected central shaft portion, which is cut to length by the surgeon, and is used in one of two modes: (a) when the footplate of the stapes is left in the oval window, a small hole is drilled through it for receiving the shaft of the prosthesis, thus assuring a close fit; or (b) if the footplate is removed, a vein, tissue or fascia graft is sized and placed over the oval window and the shaft of the prosthesis is placed in the center of the graft. (2) When only the malleus and incus are removed, and the stapes remains, the prosthesis need only span between the tympanum and the free end (capitulum) of the stapes and thus is called a partial ossicular replacement prosthesis. This device is constructed in the same manner as the total device except that the shaft portion is shorter and typically has either a tubular or inverted cup-shaped end portion which fits over the capitulum of the stapes.

Frequently, the surgeon encounters situations where the surface of the tympanum is not exactly parallel with the surface against which the tip of the shaft portion of the prosthesis must rest or fit into. Because it is important to the success of the implantation that the pressure exerted by the head portion of the prosthesis upon the tympanum be uniform throughout, the surgeon, in such case, will forcibly bend the shaft portion of the device in an attempt to compensate for the difference in angulation. The movable joint of the present invention eliminates the need to bend the the device, which could set up stresses that would cause dislodgment at either end, or penetration of tissue (the tympanum) within the middle ear (called extrusion) as a result of uneven forces set up in the device.

SUMMARY OF THE INVENTION

The present invention overcomes the problems associated with rigidly constructed ossicular replacement prostheses by providing a movable joint between the head portion and the shaft portion of the prosthesis. This construction facilitates implantation of the prosthesis and results in improved functioning after implantation; it also makes convenient the advantageous use of different materials in the prosthesis.

More specifically, the present invention provides, in a middle ear ossicular replacement prosthesis having a head portion and a shaft portion, the improvement comprising a movable joint connecting the head portion and the captured end of the shaft portion to permit pivotal movement of the shaft portion relative to the head portion in at least one plane. Preferably, the movable joint is a ball-and-socket joint with the ball portion integrally formed on the captured end of the shaft portion and with the socket portion of the joint integrally formed with the head portion. This arrangement permits universal pivotal movement of the shaft portion relative to the head portion.

In one embodiment of the invention, the shaft portion includes a free end portion constructed of porous material adapted to ingrowth of living tissue. In this same embodiment or separately, the head portion may be constructed of the same porous material, thereby allowing tissue ingrowth and enhancing stabilization of the prosthesis after implantation. In the embodiment of the invention employing a ball-and-socket joint, the socket likewise will be formed of the same porous material when it is integrally formed with the head portion. In any of the foregoing embodiments, the captured end portion of the shaft portion advantageously may be constructed of a solid material adapted to inhibit ingrowth of living tissue. On the other hand, the entire prosthesis advantageously may be constructed of the porous material, as described above.

Other features and advantages of the present invention will become apparent as the following detailed description, taken with the accompanying drawings, proceeds.

BRIEF DESCRIPTION OF THE DRAWINGS

FIG. 2 is an enlarged diagram similar to FIG. 1 with the natural sound-transmitting mechanism removed and an embodiment of the present invention substituted therefor;

FIG. 3 is similar to FIG. 2 with an alternate embodiment of the present invention shown;

FIG. 4 is an elevational view of one embodiment of the present invention, illustrating the relative movement of its parts;

FIG. 5 is a right end elevational view of the embodiment shown in FIG. 4;

FIG. 6 is a side view, partly in section, of the head portion of the embodiment shown in FIG. 5, taken along line VI—VI thereof;

FIG. 7 is an elevational view of the shaft portion of the present invention, illustrating alternate construction features; and FIG. 8 is a partial elevational view of the end portion of a still further embodiment of the present invention for use in situations similar to those shown in FIG. 2.

DESCRIPTION OF THE PREFERRED EMBODIMENTS

Figure 1:
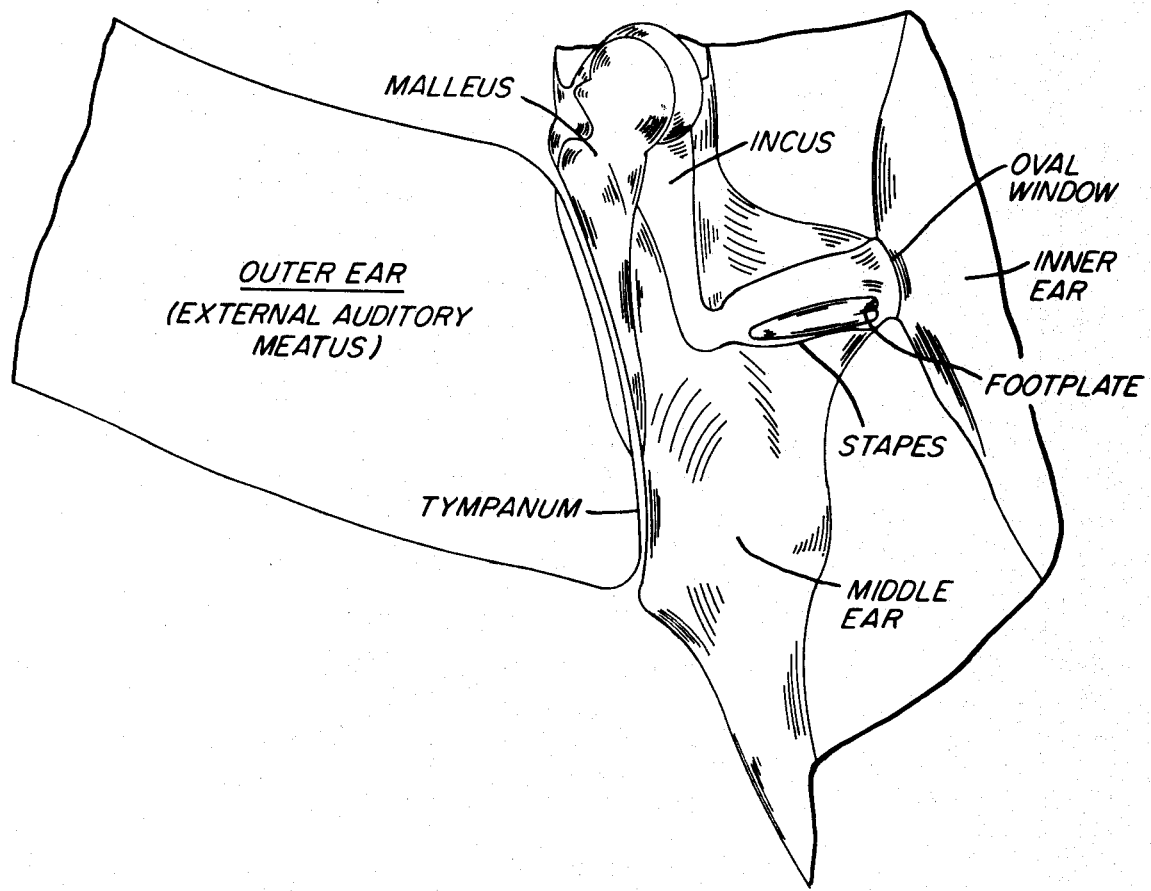
FIG. 1 is a diagram illustrating the sound-transmitting mechanism of a human ear.

Referring to the drawings, particularly to FIG. 2, there is shown a total ossicular replacement prosthesis 10 surgically implanted in the middle ear after the malleus, incus and stapes are removed. Prosthesis 10 includes a head portion 12 resting on the tympanum 14 and a shaft portion 16 whose free end rests, as previously indicated, either on a graft placed over the oval window or in a hole drilled into the remaining footplate 18 of the stapes. Head portion 12 and shaft portion 16 are connected by a movable joint 20, described in detail below, which permits accommodation of any difference in angulation (exaggerated in FIG. 2) between the surface of tympanum 14 and the surface of footplate 18.

By reason of movable joint 20, which permits shaft 16 to pivot in at least one plane normal to the plane of head 14, the flat top surface of head 12 can rest evenly on tympanum 14 and exert only minimal pressure thereon. Similarly, the free end of shaft 16 may rest on footplate 18 free of pressures that may tend to dislodge it from contact with footplate 18. With prosthesis 10 thus in place and the pressures at its contact points evenly distributed, prosthesis 10 is free to move smoothly in response to movement of tympanum 14 and thereby perform the function of transmitting sound-producing vibrations to the inner ear. Movable joint 20 contributes significantly to the transmission process by its being able to move and thereby compensate for misaligned forces generated within either head 12 or shaft 16. Absent movable joint 20, such forces may tend to dislodge the prosthesis or produce harmful point pressures on the tissue in contact with it.

FIG. 3 shows the movable joint 20 of the present invention in use with a partial ossicular replacement prosthesis 22. In contrast to FIG. 2, FIG. 3 illustrates a procedure wherein only the malleus and incus bones are removed from the middle ear. Shaft portion 24 of prosthesis 22 need extend in this situation only to the capitulum 25 of stapes 26 which is left intact. Partial prosthesis 22 typically includes a tubular or cup-shaped section at the free end of shaft portion 24 to receive the capitulum 25 of stapes 26. Nevertheless, misalignment of the surface of tympanum 14 and capitulum 25 can occur and, therefore, movable joint 20 provides the same advantages during and after surgical implantation as those described above for a total replacement prosthesis.

Turning now to construction details, a preferred embodiment of total ossicular replacement prosthesis 10 will now be described. It will be understood that insofar as movable joint 20 is concerned, the principles of construction and advantages set forth herein apply equally to total and partial ossicular replacement prostheses. Referring to FIGS. 4-6, prosthesis 10 includes a broad, thin head portion 12 having integrally formed on one side thereof a central socket 30. Socket 30, with its spherically-shaped recess 31, is adapted to receive a ball portion 32, formed on one end of shaft portion 16, to complete a conventional ball-and-socket joint between head portion 12 and shaft portion 16.

In typical dimensions, head portion 12 has a diameter of 0.156 inches and a thickness of 0.012 inches; socket 30 has an outer diameter of 0.093 inches and its recess 31 has a spherical radius of 0.0315 inches to receive ball portion 32 which has a spherical radius of 0.031 inches; the total depth of socket 30 is 0.039 inches, thereby providing an overlap of 0.0075 inches of socket 30 over ball portion 32. So dimensioned, shaft 16 is universally pivotal about socket 30 with a maximum range of motion of about 90° in any plane normal to head 12, or about 45° on either side of perpendicular. The range of motion of shaft 16 may be increased or decreased by adjusting the amount of overlap of socket 30 over ball portion 32.

Shaft portion 16 is constructed of a solid cylindrical member with ball portion 32 integrally formed thereon. In typical dimensions, shaft 16 has a length, measured from the center of ball portion 32, of 0.272 inches and a diameter of 0.0315 inches. Shaft 16 is adapted to be cut to proper length by the surgeon during implantation of prosthesis 10 to custom fit the patient.

It will be appreciated by those skilled in the art that a variety of well-known means may be employed to form movable joint 20 between head portion 12 and shaft portion 16 of prosthesis 10; the only requisite is to provide pivotal relative movement of shaft 16 in at least one plane normal to head 12. Included in such possible means are an elbow joint, a hinge joint, a partially surrounded cylinder, a flatened ball and socket, and a reversed ball and socket. Any of these joints, including the ball-and-socket described above, may be formed off-center with respect to head 12 if desired. Although perhaps less desirable because of the restricted movement afforded between shaft and head, prosthesis 10 may be formed in one piece with a flexible "living hinge" joining head portion 12 and shaft portion 16. Depending upon the elastic properties of the material used to form the living hinge, such construction may not, however, afford significant advantages over the prior art one-piece devices.

Head portion 12 is shown in the drawings as being round; it could also be oval, square, rectangular or triangular depending upon the particular application. Likewise, shaft portion 16 is shown to be of round cross section, but it could be formed with its free end portion having an oval cross section to better conform to the shape of the oval window in the middle ear. Socket 30 is shown centrally located with respect to head portion 12; socket 30 may be offset, however, if the structure of the particular inner ear warrants it.

A variety of materials may be used to form prosthesis 10; the only critical criteria are corrosion-resistance and biocompatibility. Metals, such as stainless steel, chrome-cobalt alloys, platinum, or titanium may be employed with the component parts being formed by machining and/or powder metallurgy techniques. Ceramic materials may also be used. Synthetic resins, however, are the preferred materials, primarily because of their moldability and cost; these include silicones. Teflon phenolics and preferably polyethylene and polypropylene. Any of the foregoing materials may be solid or porous, the selection being governed by factors discussed below.

In view of the fact that both ends of prosthesis 10, when implanted, are in contact with living tissue, it is desirable to promote growth of that tissue in and around those ends to enhance adhesion of the implant and its vibration-transmission capability. Accordingly, it is advantageous to form at least head portion 12 and the end portion of shaft 16 of porous material that permits such ingrowth; under some circumstances, the entire prosthesis 10 may be formed of such porous material. A particularly useful porous material for use in the present invention is a high molecular weight polyethylene sponge marketed by Richards Manufacturing Company, Memphis, Tennessee under the trademark "Plastipore"; this material is highly nonreactive with body tissue and is 70 to 90% porous with an average pore size of 250 microns, which is sufficient to encourage tissue ingrowth. Plastipore ® is relatively rigid and thus lends itself to machining into a variety of shapes.

In one embodiment, prosthesis 10 may be constructed so that head 12 and socket 30 are formed of porous polyethylene. With the top surface of head 12 in contact with tympanum 14, tissue ingrowth into head 12 will tend to stabilize it in broad contact with tympanum 14. As may be seen in FIG. 7, shaft 16 may be formed in two parts in this embodiment; the left portion including ball portion 32 is formed of solid polyethylene and the right portion 36 is formed of porous polyethylene. The porous polyethylene portion 36 is bonded to the solid portion of shaft 16 in abutting relationship by mechanical, thermal and/or chemical techniques that are well-known in the art. With porous polyethylene section 36 in contact with footplate 18 or grafted tissue (or with the stapes capitulum in a partial replacement), tissue ingrowth into porous portion 36 is encouraged with the same stabilizing effects as described for head portion 12.

An advantage of the use of two materials to form shaft 16 is that the solid portion including ball portion 32 resists tissue ingrowth and thus tends to assure continuing smooth movement of ball portion 32 within socket 30. When two such materials are employed, color coding of each section may aid the surgeon in distinguishing the parts although porous section 36 always will be of such length as to accommodate substantially all potential patients even with trimming as described above.

A possible further adaption of the present invention in total replacement situations is to connect a second head portion at the free end of shaft 16 by means of a second ball-and-socket joint. This technique would afford broad surface contact with the interface to the inner ear and a resultant improvement in the sound-transmission properties of the prosthesis. The second head portion could be oval-shaped to fit into the oval window and thus could eliminate the necessity of a tissue or vein graft when the footplate is removed.

FIG. 8 illustrates an alternate embodiment of the shaft portion of partial ossicular replacement prosthesis 22'. As discussed above in connection with FIG. 3, it is desirable to provide means at the free end of such a prosthesis for receiving the capitulum of the stapes. FIG. 8 shows a cup-shaped portion 40 formed on the free end of shaft portion 24' to accomplish this purpose. Cup-shaped portion 40 may include openings 42, formed 90° from one another, which promote tissue ingrowth therethrough.

What is claimed is:

1. In a middle ear ossicular replacement prosthesis having a head portion and a shaft portion, the improvement comprising:
a movable joint connecting said head portion and the captured end of said shaft portion to permit pivotal movement of said shaft portion relative to said head portion, said movable joint being a ball-and-socket joint which permits universal pivotal movement of said shaft portion relative to said head portion.

2. The improvement recited in claim 1 wherein:
said prosthesis is constructed of porous material adapted to ingrowth of living tissue.

3. The improvement recited in claim 1 wherein:
said ball portion of said joint is integrally formed on said captured end of said shaft portion and said socket portion of said joint is integrally formed with said head portion.

4. The improvement recited in claim 1 wherein:
said shaft portion includes a free end portion constructed of porous material adapted to ingrowth of living tissue.

5. The improvement recited in claim 1 wherein:
said head portion is constructed of porous material adapted to ingrowth of living tissue.

6. The improvement recited in claim 5 wherein:
said ball-and-socket joint has its socket portion integrally formed with said head portion and constructed of porous material adapted to ingrowth of living tissue.

7. The improvement recited in any one of claims 4, 5 or 6 wherein:
said captured end portion of said shaft portion is constructed of a solid material adapted to inhibit ingrowth of living tissue.

* * * * *

UNITED STATES PATENT AND TRADEMARK OFFICE
CERTIFICATE OF CORRECTION

PATENT NO. : 4,281,419

DATED : August 4, 1981

INVENTOR(S) : Harry T. Treace

It is certified that error appears in the above–identified patent and that said Letters Patent are hereby corrected as shown below:

Col. 4, line 52, delete "silicones. Teflon phenolics" and substitute therefor --silicones, Teflon, phenolics--.

Signed and Sealed this

Third Day of November 1981

[SEAL]

Attest:

GERALD J. MOSSINGHOFF

Attesting Officer     Commissioner of Patents and Trademarks